(12) United States Patent
Jin et al.

(10) Patent No.: US 9,314,492 B2
(45) Date of Patent: *Apr. 19, 2016

(54) **COMPOSITION FOR CANCER PREVENTION OR TREATMENT CONTAINING AS ACTIVE INGREDIENT PLANT STEM CELL LINE DERVIED FROM CAMBIUM OF *PANAX GINSENG* INCLUDING WILD GINSENG OR GINSENG**

(75) Inventors: Young Woo Jin, Jeonbuk (KR); Eun Kyong Lee, Jeonbuk (KR)

(73) Assignees: UNHWA CORPORATION, Jeonju-Si, Jeollabuk-Do (KR); Young Woo Jin, Jeonju-Si, Jeollabuk-Do (KR); Eun Kyoung Lee, Jeonju-Si, Jeollabuk-Do (KR)

( * ) Notice: Subject to any disclaimer, the term of this patent is extended or adjusted under 35 U.S.C. 154(b) by 129 days.

This patent is subject to a terminal disclaimer.

(21) Appl. No.: 13/127,750

(22) PCT Filed: Nov. 6, 2009

(86) PCT No.: PCT/KR2009/006523
§ 371 (c)(1),
(2), (4) Date: Jun. 10, 2011

(87) PCT Pub. No.: WO2010/053314
PCT Pub. Date: May 14, 2010

(65) Prior Publication Data
US 2011/0229443 A1 Sep. 22, 2011

(30) Foreign Application Priority Data
Nov. 6, 2008 (KR) .......................... 10-2008-0110086

(51) Int. Cl.
*A01N 65/00* (2009.01)
*A61K 36/258* (2006.01)
*A01H 4/00* (2006.01)
*A23L 1/30* (2006.01)
*C12N 5/04* (2006.01)

(52) U.S. Cl.
CPC .............. *A61K 36/258* (2013.01); *A01H 4/005* (2013.01); *A23L 1/3002* (2013.01); *C12N 5/04* (2013.01); *A23V 2002/00* (2013.01)

(58) Field of Classification Search
CPC ...... A61K 36/258; C12N 5/04; A23L 1/3002; A23V 2002/00
See application file for complete search history.

(56) References Cited

U.S. PATENT DOCUMENTS

| 4,795,742 | A * | 1/1989 | Liu .................................. 514/26 |
| 6,911,221 | B2 * | 6/2005 | Li .................................. 424/728 |
| 8,017,397 | B2 | 9/2011 | Jin et al. |
| 8,053,238 | B2 | 11/2011 | Jin et al. |
| 8,247,230 | B2 | 8/2012 | Jang et al. |
| 2003/0190378 | A1 * | 10/2003 | Kim et al. .................. 424/728 |
| 2006/0034951 | A1 | 2/2006 | Kwak et al. |
| 2010/0233813 | A1 * | 9/2010 | Jang et al. .................. 435/420 |
| 2010/0255585 | A1 | 10/2010 | Yu et al. |
| 2010/0272692 | A1 | 10/2010 | Park et al. |
| 2011/0117039 | A1 | 5/2011 | Lee et al. |

FOREIGN PATENT DOCUMENTS

| KR | 100456089 B1 | 11/2004 |
| KR | 100478213 B1 | 3/2005 |
| KR | 100533120 B1 | 12/2005 |
| KR | 100594353 B1 | 7/2006 |
| WO | WO 2007052876 A1 * | 5/2007 |

OTHER PUBLICATIONS

Prevent—defined by Merriam-Webster online dictionary, at the web http://www.merriam-webster.com/dictionary/prevent; pp. 1-2, accessed on Mar. 24, 2013.*
ACS 2008: Ginseng—web publication from Americal Cancer Society (ACS) published on Nov. 28, 2008 at the web at-(http://www.cancer.org/treatment/treatmentsandsideeffects/complementaryandalternativem..); pp. 1-3.*
MEDLINEPLUS 2012 web publication—Ginseng, PANAX; last reviewed and published on Dec. 11, 2012 on the web at-(http://www.nlm.nih.gov/medlineplus/druginfo/natural/1000.html), pp. 1-10.*
Kubo M. et al., Histochemistry. I. Ginsenosides in ginseng (Panax ginseng C. A. Meyer, root), J. Nat. Prod., vol. 43, No. 2, pp. 278-284.*
Bulgakov V.P. et al., Chromosome Variation in Ginseng Cells Transformed with the roIC Plant Oncogene, Russian Journal of Genetics, 2000, vol. 36, No. 2, pp. 150-156.*
Xiaojie et al., Fungal Elicitor Induces Singlet Oxygen Generation, Ethylene Release and Saponin Synthesis in Cultured Cells of Panax ginseng C. A. Meyer, Plant Cell Physiology, 2005, vol. 46, No. 6, pp. 947-954.*
Wu J. et al., Production of ginseng and its bioactive components in plant cell culture: Current technological and applied aspects, journal of Biotechnology, 1999, vol. 68, pp. 89-99.*
FAO 2001 (cited as ref. [X] on PTO 892)—Approaches to increase productivity, FAO Corporate Document Repository, Plant tissue culture: an alternative for production of useful metabolite, published on Feb. 1, 2001 (http://www.fao.org/docrep/t0831e/t0831e07.htm), pp. 1-14.*

(Continued)

*Primary Examiner* — Satyendra K Singh
(74) *Attorney, Agent, or Firm* — Tristan A. Fuierer; Moore & Van Allen, PLLC (57) ABSTRACT

The present invention relates to a composition for preventing or treating cancer, which contains, as an active ingredient, a *Panax ginseng* cambium-derived cell line including wild ginseng or ginseng; a lysate thereof; an extract thereof; or a culture medium thereof, which are derived from a natural and have minimized side effects compared to the conventional therapeutic drugs, and thus are safe for the human body. Also, they are involved directly in the growth of cancer to induce cancer cell death effectively, and show anticancer activity of inhibiting or reducing the formation of tumor or the growth of tumor.

8 Claims, 4 Drawing Sheets

(56) References Cited

OTHER PUBLICATIONS

Kamangar, Farin, et al.; "Ginseng Intake and Gastric Cancer Risk in the Shanghai Women's Health Study Cohort,"Cancer Epidemiology Biomarkers and Prevention, 2007, pp. 629-630, vol. 16.

Shibata, Shoji; "Chemistry and Cancer Preventing Activities of Ginseng Saponins and Some Related Triterpenoid Compounds," J. Korean Med. Sci, 2001, pp. S28-S37, vol. 16.

Yun, Taik-Koo, et al.; "Epidemiological Study on Cancer Prevention by Ginseng: Are All Kinds of Cancers Preventable by Ginseng?" J. Korean Med. Sci., 2001, pp. S19-S27, vol. 16.

International Search Report, Jun. 21, 2010.

Kim et al., Antioxidant activity and functional component analysis of Korean mountain ginseng's different sections, J. Korean Soc. Food Sci. Nutr., 2006, vol. 35, pp. 1315-1321.

Shi et al., Investigation of ginsenosides in different parts and ages of Panax ginseng, Food Chemstry, 2007, vol. 102, pp. 664-668.

Wang et al., Antiproliferative effects of different plant parts of Panax notoginseng on SW480 human colorectal cancer cells, Phytotherapy Research, 2009, vol. 23, pp. 6-13.

Hwang et al., Quantitative analysis of phenolic compounds in different parts of Panax ginseng C.A. Meyer and its inhibitory effect on melanin biosynthesis, Korean J. Medicinal Crop Sci., 2006, vol. 14, pp. 148-152.

Lee et al., Antioxidant activities of leaf, stem, and root of Panax ginseng C.A. Meyer, Korean J. Medicinal Crop Sci., 2004, vol. 12, pp. 237-242.

* cited by examiner

| | mg/ml | |
|---|---|---|
| | U2 | Cultured root of wild ginseng |
| MDA-MB-231 (Breast cancer) | 0.47 | 0.99 |
| AsPC-1 (Pancreatic cancer) | 0.39 | 1.0 |
| DU-145 (Prostate cancer) | 0.32 | 2.0 |
| A549 (Lung cancer) | 0.17 | 3.85 |
| A375P (Melanoma) | 0.28 | 1.46 |
| HeLa (Cervical cancer) | 0.39 | 5.92 |
| SK-Hep1 (HCC) | 0.4 | 6.28 |
| HT-29 (Colon cancer) | 0.47 | - |

COMPOSITION FOR CANCER PREVENTION OR TREATMENT CONTAINING AS ACTIVE INGREDIENT PLANT STEM CELL LINE DERVIED FROM CAMBIUM OF *PANAX GINSENG* INCLUDING WILD GINSENG OR GINSENG

CROSS-REFERENCE TO RELATED APPLICATIONS

This application is a U.S. national phase of International Application No. PCT/KR2009/006523 filed on Nov. 6, 2009, which claims the benefit of Korean Application No. 10-2008-0110086 filed on Nov. 6, 2008, the contents of which are hereby incorporated by reference in their entirety.

TECHNICAL FIELD

The present invention relates to a composition for preventing or treating cancer, which contains, as an active ingredient, a *Panax ginseng* cambium-derived cell line; a lysate thereof; an extract thereof; or a culture medium thereof.

BACKGROUND ART

Cancer is one of diseases that occupy the leading cause of death of the modern people and is caused by mutations in genes that regulate normal cell growth. It is defined as a malignant tumor that does not follow normal cell differentiation and growth patterns.

Traditionally, cancer has been treated by one or a combination of three major therapies: surgery, radiotherapy and chemotherapy. Specifically, the cancer treatment with surgery, i.e., a method of removing tumor tissue, is very effective in removing tumors from specific sites, for example, breast, colon and skin. However, it is not suitable for treating either tumors present in a site such as the vertebra or dispersible tumors. In some cases, such a surgical therapy encounters a problem in that adverse effects such as organ removal and tumor metastasis cannot be prevented.

Meanwhile, the radiotherapy is used for acute inflammatory diseases, benign or malignant tumors, endocrine dysfunction, allergic diseases and the like. Generally, such a radiotherapy is effectively used for malignant tumors consisting of cells that divide rapidly. However, this radiotherapy can result in a weakness or loss of the function of normal tissue and a cause of skin diseases in the treatment sites to which it had been applied. In addition, in case of infants in which the development of organs progresses, the radiotherapy can cause serious adverse effects, such as mental retardation or bone growth disorders. Further, it gives a pain to a patient during treatment.

Similarly, the chemotherapy is also widely used to treat breast, lung and testicle cancers by disturbing the replication or metastasis of cancer cells. However, it is known that anticancer agents exhibit toxicity not only against cancer cells but also against normal cells of a patient. In addition, such a chemotherapy generally suffers from disadvantages in that hospital treatment is required in severe cases or an analgesic needs to be used to relieve a pain.

Thus, many studies on the development of new drugs and formulations having anticancer activity, which inhibit cancer cell growth and kill cancer cells, have been conducted. In particular, studies on the development of anticancer agents derived from natural materials, which have little side effects, have received a great deal of attention.

Accordingly, the present inventors have made many efforts to develop a natural material-derived anticancer composition, which has minimized side effects compared to conventional anticancer agents and exhibits excellent anticancer activity through its involvement in the mechanism of development of cancer. As a result, the present inventors have found that a homogeneous cell line derived from the cambium of *Panax ginseng* including wild ginseng or ginseng, a lysate thereof, an extract thereof and a culture thereof show cancer cell-killing activity, thereby completing the present invention.

SUMMARY OF INVENTION

It is an object of the present invention to provide a natural material-derived composition, which has minimized side effects compared to the conventional therapeutic agent for cancer and shows activity for preventing and treating cancer.

To achieve the above object, in one aspect, the present invention provides a pharmaceutical composition for preventing or treating cancer, which contains any one or more selected from the group consisting of a cell line, which is derived from the cambium of *Panax ginseng* and has the following characteristics; a lysate thereof; an extract thereof; and a culture medium thereof:

(a) it is in an innately undifferentiated state; and
(b) it is morphologically characterized by multiple vacuoles.

In another aspect, the present invention provides a functional food for preventing cancer or improving cancer condition, which contains any one or more selected from the group consisting of said cell line; said lysate; said extract; and said culture medium.

In still another aspect, the present invention provides the use of any one among said cell line, said lysate; said extract; and said culture medium to prevent or treat cancer.

In yet another aspect, the present invention provides a method for preventing or treating cancer, the method comprises using any one or more selected from the group consisting of said cell line; said lysate; said extract and said culture medium.

Other features and embodiments of the present invention will be apparent from the following detailed description and the appended claims.

DETAILED DESCRIPTION OF THE INVENTION AND PREFERRED EMBODIMENTS

Unless otherwise defined, all technical and scientific terms used herein have the same meaning as commonly understood by one of ordinary skill in the art. Generally, the definitions of various terms used herein are well known and conventionally used in the art.

The definition of main terms used in the detailed description of the invention is as follows.

As used herein, the term "cambium" refers to a tissue that thickens the stem and root to allow the plant grow volumetrically. It was reported that when the cambium, a meristem where the most active cell division occurs, is used as an explant for plant tissue culture, rapid and mass production of cells is possible (Korean Patent 10-0533120).

As used herein, the term "lysate" refers to a cell lysate obtained by disrupting cells through a chemical method with, for example, a detergent, or a physical method. The term "extract" of a cell line refers to a substance obtained by dissolving cells in a solvent and isolating the cells, and the extract can be concentrated through distillation or evaporation. Herein, cell line is intended to include a cell line which goes through differentiation under culture conditions or which has improved ability to produce and/or secrete useful substances. The term "culture medium" of the cell line as used herein refers to cell culture medium in which the cell line was removed after cell culture.

As used herein, the term "innately undifferentiated" means that cells are not present in an undifferentiated state through a dedifferentiation process, but are originally maintained in a pre-differentiated state.

In one aspect, the present invention provides a composition for preventing or treating cancer, which contains, as an active ingredient, any one or more of a cell line derived from the cambium of *Panax ginseng*, a lysate thereof, an extract thereof and a culture medium thereof. In the present invention, *Panax ginseng* includes wild ginseng or ginseng (Lian M. L. et al., *J. Plant Biology*, 45: 201, 2002; Han J. Y. et al., *J. Plant Biology*, 49:26, 2006; Teng W. L. et al., *Tissue and Organ Culture*, 68:233, 2002). In the present invention, the wild ginseng or ginseng includes open field true wild ginseng or tissue-cultured ginseng (adventitious root and adventitious root-derived cell line).

The *Panax ginseng* cambium-derived cell line according to the present invention has the following characteristics: (a) it is in an innately undifferentiated state; and (b) it is morphologically characterized by a number of vacuoles. The *Panax ginseng* cambium-derived cell line according to the present invention is additionally characterized in that: (a) it is present as single cell level during suspension culture; (b) it has low sensitivity to shear stress in a bioreactor compared to cell lines derived from tissues other than the cambium of *Panax ginseng*, and (c) it has a higher growth rate than those of cell lines derived from tissues other than the cambium or *Panax ginseng* and is cultured stably. In addition, the cell line is homogeneous.

In the present invention, wherein cell line is obtained using an isolation method comprising the steps of: (a) obtaining tissue containing the cambium of *Panax ginseng*; (b) culturing the obtained cambium-containing tissue in a medium containing indole-3-acetic acid (IAA) or indole-3-butyric acid (IBA), thereby inducing a cambium-derived cell line, wherein osmotic stress is applied to the cambium-containing tissue during, before or after the culture; and (c) collecting the induced cambium-derived cell line.

In step (b) of the inventive method, the application of osmotic stress is carried out in order to induce the cell line specifically in the cambium. Preferably, it is carried out before culturing the tissue in the IAA- or IBA-containing medium, such that general tissues (i.e., cortex, phloem, xylem and pith) other than the cambium lose the ability to divide, and thus become necrotic when they are treated with a cambial division-specific hormone such as IAA or IBA. Herein, preferably, the osmotic agent is used in an amount of 0.5-2M, and the osmotic stress is applied in a cold state or at room temperature for 16-24 hours, and then removed. However, the scope of the present invention is not limited thereto, because the concentration, treatment time and temperature of the osmotic agent may vary depending on the kind of plant and the state of tissue. In the step (b), IAA or IBA is preferably contained in an amount of 0.1-5 mg/l.

In addition, wherein the step (c) is preferably carried out by proliferating the induced cambium-derived cell line in a medium containing one or more of 2,4-D (2,4-dichlorophenoxyacetic acid; picloram and IBA; and then collecting the cambium-derived cell line. Herein, any one of 2,4-D, picloram and IBA is preferably used in an amount of 1-5 mg/L, and more preferably 2 mg/L.

The medium used in the present invention is a conventional medium for plant tissue culture, and examples thereof may include, but are not limited to, N6 medium, SH medium, MS medium, AA medium, LS medium, B5 medium, WPM medium, LP medium, White medium, GD medium, DKW medium, DCR medium, etc.

In the present invention, the extract is preferably obtained using a solvent selected from the group consisting of distilled water, alcohol such as lower alcohol or the like, acetone, DMSO (dimethyl sulfoxide) and mixed solvents thereof. Herein, examples of the lower alcohol include alcohols having 1 to 5 carbon atoms, such as methanol and ethanol.

In one Example of the present invention, pancreas cancer, lung cancer, liver cancer, colon cancer, breast cancer, cervical cancer, skin cancer and prostate cancer cell lines were treated with *Panax ginseng* cambium-derived cell line extract according to the present invention. As a result, it was observed that the cell line extract according to the present invention has cancer cell-killing activity on all of cancer cell lines. Also, in another Example of the present invention, it was observed that culture medium of *Panax ginseng* cambium-derived cell line according to the present invention has cancer cell-killing activity on breast cancer and pancreas cancer cell lines.

In addition, in still another Example of the present invention, *Panax ginseng* cambium-derived cell line according to the present invention was administered to a patient diagnosed with cancer (e.g., lymphoma, lung cancer, rectal cancer and gastric cancer etc.) and then PET-CT image was obtained. As a result, it was observed that the *Panax ginseng* cambium-derived cell line inhibited or reduced the formation of tumor or the growth of tumor by killing cell lines in vivo (e.g., patient), and blood levels were measured after *Panax ginseng* cambium-derived cell line according to the present invention was administered to a patient diagnosed with leukemia. As a result, it was observed that blood levels became normal. In other words, the cell line according to the present invention were effective for the prevention and treatment of pancreas cancer, liver cancer, colon cancer, breast cancer, cervical cancer, skin cancer, prostate cancer, lymphoma, leukemia, lung cancer, rectal cancer and gastric cancer, but not limited thereto.

Accordingly, it was found as described above that the cell lines, extracts thereof and culture medium had activity for preventing and treating cancer. Thus, even though in the present invention, there is no specific example showing that a composition containing a lysate of the cell line shows the effect of preventing and treating cancer, it will be obvious to those skilled in the art that the composition containing the lysate of the cell line according to the present invention can also show the effect of preventing and treating cancer.

A composition for preventing or treating cancer, containing any one or more of the cell line according to the present invention; a lysate thereof; an extract thereof; and culture medium thereof, may be provided as a pharmaceutical composition containing any one or more selected from the group consisting of the cell line; the lysate thereof, the extract thereof; and the culture medium thereof alone or in combination with at least one pharmaceutically acceptable carrier, excipient or diluent. The cell line, the lysate thereof, the extract thereof or the culture medium thereof may be contained as pharmaceutical composition in a pharmaceutically effective amount depending on disease and its severity, the patient's age, weight, health condition and sex, the route of administration and the period of treatment.

As used herein, the term "pharmaceutically acceptable composition" refers to a composition that is physiologically acceptable and does not cause gastric disorder, allergic reactions such as vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of powders, granules, tablets, emulsions, syrups, aerosols, soft or hard gelatin capsules, sterile injection solutions, sterile powders, etc.

In another aspect, the present invention provides a functional food for preventing cancer or improving cancer condition, which contains any one or more selected from the group consisting of said cell line derived from the cambium of *Panax ginseng*; the lysate thereof, the extract thereof; and the culture medium thereof.

As used herein, the term "functional food" refers to a food, the functionality of which has been improved by adding the cell line according to the present invention, the lysate thereof or the extract thereof.

EXAMPLES

Hereinafter, the present invention will be described in further detail with reference to examples. It will be obvious to those skilled in the art that these examples are illustrative purpose only and are not to be construed to limit the scope of the present invention, Particularly, although the cancer preventive effects and cancer inhibitory effects of the wild ginseng cambium-derived cell line, the extract thereof and the culture medium thereof were confirmed in the following examples, it will be obvious to those skilled in the art that the use of a lysate of the cell line can provide the same results as those obtained using the cell line or the extract thereof.

Example 1

Preparation of Cell Line Derived from Cambium of *Panax ginseng*

Figure 1:
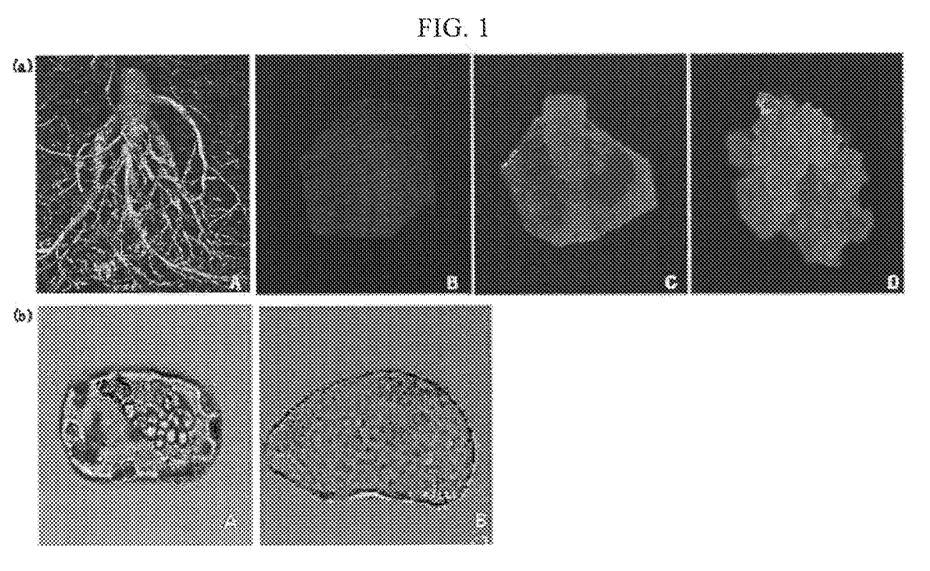
FIG. 1(a) is a set of photographs showing a process of inducing a wild ginseng cambium-derived cell line according to the present invention.
FIG. 1(b) is a set of photographs showing a process of inducing a ginseng cotyledon-derived callus cell line (biological resource center KCTC PC10224).

1-1: Preparation of Plant Material (1) "A" of FIG. 1(a) shows the typical feature of wild ginseng used in the present invention. In order to use the main root of purchased wild ginseng, the main root was purchased, and then washed with running water to remove earth or other contaminants from the surface thereof, and the surface of the main root was washed with a liquid detergent. Then, the main root was allowed to stand under running water. The washed root tissue was placed in a sterilized flask in a clean bench and disinfected with 70% ethanol for a time ranging from about 30 seconds to about 1 minute. Then, it was rinsed with sterilize distilled water and treated with a disinfectant solution containing 1-1.5% sodium hypochlorite (Junsei, Japan) for about 5-15 minutes. At this time, in order to allow the disinfectant solution to effectively penetrate into the tissue, several drops of TWEEN 20 (polyoxyethylenesorbitan monolaurate, Junsei, Japan) were added. Following this, the tissue was rinsed 3-5 times with sterilize distilled water. In order to prevent browning of the disinfected tissue, the disinfected main root was placed in antioxidant-containing BIM (browning inhibition medium) and shake-cultured for about 30 minutes to 1 hour. Then, the tissue was placed on sterile filter paper to remove water.

The composition of BIM used and the concentrations of components thereof are shown in Table 1 below.

TABLE 1

| Composition of BIM and concentrations of components thereof | |
|---|---|
| Composition | Concentrations |
| McCown WPM salt | ¼ strength |
| Sucrose | 1% (w/v) |
| PVP (polyvinyl pyrrolidone) | 0.5% (w/v) |
| Ascorbic acid | 100 mg/L |
| Citric acid | 150 mg/L |

Adjust to pH 5.8

Here, the salt is added in an amount corresponding to ¼ of the total amount.

Then, in order to prevent the above treated material from browning, the material was placed in a sterilzed petri dish containing an antioxidant-containing CS solution (cutting solution, Table 2) and peeled. Then, the material was cut into two equal parts, and each of the parts was cut to a size of 0.5-0.7 cm (width)×0.5-0.7 cm (length)×0.2-0.5 mm (thickness) in such a manner that each cut portion contained a cambium portion having active division ability. "B" of FIG. 1(a) shows the explant prepared by cutting the main root of the wild ginseng to the above size in such a manner that the explant contains the cambium.

TABLE 2

| Component | Concentrations |
|---|---|
| CS (cutting solution) | |
| PVP (Polyvinyl pyrrolidone) | 0.5% (w/v) |
| Ascorbic acid | 100 mg/L |
| Citric acid | 150 mg/L |

(2) The adventitious root of 100-year-old wild ginseng that was being maintained in a bioreactor was prepared and placed in a sterilzed petri dish containing the CS solution of Table 2, and an explant containing the cambium of the wild ginseng root was obtained in the same manner as described above.

1-2: Treatment of Explant Containing Cambium of Main Root of Wild Ginseng with Osmotic Agent The explant prepared in Example 1-1 was treated with osmotic stress in order to necrotize differentiated tissues (i.e., phloem, xylem, pith, etc.) and to allow only the meristem cambium to survive. The cambium-containing explant was blotted onto a pre-culture medium (medium 1, Table 3) having filter paper laid thereon, and it was placed in a flask containing 1M sucrose solution (Duchefa, Netherland) and was treated with osmotic stress in a cold state for 16-24 hours.

Then, the explant was treated in 0.05M sucrose solution for 5 minutes and in 0.1M sucrose solution for 5 minutes to remove the stress caused by the high-concentration sucrose. The cambium-containing explant from which the osmotic stress has been removed was placed on a pre-culture medium (medium 1) having filter paper laid thereon to remove moisture.

TABLE 3

Composition of pre-culture medium (medium 1)

| | Composition | mM | mg/L |
|---|---|---|---|
| Macroelements | $Ca(NO_3)_2$ | 2.35 | 471.26 |
| | $NH_4NO_3$ | 5 | 400 |
| | $MgSO_4 \cdot 7H_2O$ | 1.5 | 180.54 |
| | $K_2SO_4$ | 5.68 | 990 |
| | $CaCl_2 \cdot 2H_2O$ | 0.65 | 72.5 |
| | $KH_2PO_4$ | 1.25 | 170 |
| | | µM | |
| Microelements | $MnSO_4 \cdot 4H_2O$ | 131.94 | 22.3 |
| | $ZnSO_4 \cdot 7H_2O$ | 29.91 | 8.6 |
| | $Na_2MoO_4 \cdot 2H_2O$ | 1.03 | 0.25 |
| | $H_3BO_3$ | 100.27 | 6.2 |
| | $CuSO_4 \cdot 5H_2O$ | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Cambium-Derived Homogeneous Cell Line in Explant Containing the Cambium of Wild Ginseng In order to induce a cambium-derived homogeneous cell line having the cell division ability, the explant treated with osmotic stress in Example 1-2 was transferred to a cell line induction medium (medium 2, Table 4). The composition of the medium used is shown in Table 5 below. The transferred explant was cultured in a dark condition at 22±1° C.

TABLE 4

Medium composition (medium 2) used to induce cambium-derived homogeneous cell line

| Component | Concentration and condition |
|---|---|
| Salt | Full strength WPM |
| Sucrose | 3% (w/v) |
| IAA (Indole-3-acetic acid) | 2 mg/L |
| pH | 5.8 |
| Gelrite | 0.3% (w/v) |
| Ascorbic acid | 100 mg/L |
| Citric acid | 150 mg/L |

As shown in Table 5 below, in the explants transferred directly onto the homogeneous cell line-induction medium without carrying out osmotic treatment, a yellow color reaction was shown with respect to the cambium at an initial stage (2-3 days) after the transfer, and then with the passage of time, the entire explant turned yellow. The explant which has showed the yellow color reaction with respect to the cambium was subcultured in an optimal medium (medium 3) for the isolation and proliferation of a cambium-derived cell line in order to induce and proliferate the cambium-derived cell line, but the browning phenomenon became severe, and any reaction other than the browning color reaction was not shown even with the passage of time.

However, after the osmotic stress was treated and removed, it was observed as shown in Table 5 that, in the explant inoculated onto the homogeneous cell line-induction medium, a homogeneous cell line was specifically induced only in the cambium without being induced in other tissues. Specifically, it was observed that, in the transferred explant which has been treated with osmotic stress and from which the osmotic stress has been released, the cambium of the explant started to turn a light yellow after 3-7 days of the culture, and after about 7-14 days therefrom, a round cell line was induced at the portion that changed to the light yellow color. Herein, the same results were observed in both the explant containing the cambium of the open field true wild ginseng and the explant containing the cambium of the wild ginseng adventitious root. "C" of FIG. 1(a) shows that the homogeneous cell line having cambium-specific division ability was induced in the explant containing the cambium of wild ginseng.

Meanwhile, the explant was cultured in a 2,4-D-containing medium, which was not the homogeneous cell line-induction medium and has been used in the conventional culture of *Panax ginseng*, including ginseng and wild ginseng. In this case, it was observed that the entire explant started to turn yellow after 7-10 days of the culture, and about 7-14 days therefrom, cells were induced throughout the whole cross section.

TABLE 5

Comparison of reaction between explant treated with osmotic stress and explant not treated with osmotic stress

| Treatment | Not treated | Treated for 16 hours | Treated for 20 hours | Treated for 24 hours |
|---|---|---|---|---|
| Aspect | After the inoculation, initially a yellow color reaction progressed starting from the cambium and then spread out throughout the whole explant. Then, a severe browning color reaction progressed | It was observed that cells were specifically induced only in the cambium. When the explant was treated with osmotic stress for varying periods of time, similar results were shown. In other words, | | |

TABLE 5-continued

Comparison of reaction between explant treated with osmotic stress and explant not treated with osmotic stress

| Treatment | Not treated | Treated for 16 hours | Treated for 20 hours | Treated for 24 hours |
|---|---|---|---|---|
| | throughout the explants including the cambium, and the induction of a homogeneous cell line, specific in the cambium, was no longer shown. | there was no significant difference between the treatment periods. | | |

1-4: Proliferation of Isolated Homogeneous Cell Line Derived from Cambium of Wild Ginseng The cambium-derived homogeneous cell line having the ability to divide, induced in Example 1-3, was allowed to proliferate. The medium used in the proliferation was an optimal medium (Table 7) for proliferation of the cambium-derived homogeneous cell line having the ability to divide, which contained a basal salt composition (Table 6). 2,4-D in Table 7 was used for the proliferation of the homogeneous cell line derived from the cambium of the open field true wild ginseng, and IBA in Table 7 was used for the proliferation of the homogeneous cell line derived from the wild ginseng adventitious root.

TABLE 6

Basal salt composition of optimal medium for the isolation and proliferation of cambium-derived homogeneous cell line having the ability to divide

| Composition | | | mg/L |
|---|---|---|---|
| | | mM | |
| Macroelements | CaCl$_2$•2H$_2$O | 2.99 | 332.02 |
| | KH$_2$PO$_4$ | 1.25 | 170 |
| | KNO$_3$ | 18.79 | 1900 |
| | MgSO$_4$ | 1.5 | 180.54 |
| | NH$_4$NO$_3$ | 20.61 | 1650 |
| | | uM | |
| Microelements | CoCl$_2$•6H$_2$O | 0.11 | 0.025 |
| | CuSO$_4$•5H$_2$O | 0.1 | 0.025 |
| | FeNa-EDTA | 100 | 36.7 |
| | H$_3$BO$_3$ | 100.27 | 6.2 |
| | KI | 5.0 | 0.83 |
| | MnSO$_4$•4H$_2$O | 100 | 16.9 |
| | Na$_2$MoO$_4$•2H$_2$O | 1.03 | 0.25 |
| | ZnSO$_4$•7H$_2$O | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 7 composition of optimal medium (medium 3) for the isolation and proliferation of cambium-derived homogeneous cell line having the ability to divide

| Component | Concentration and condition |
|---|---|
| Salt | Full strength MS |
| Sucrose | 3% (w/v) |
| IBA (Indole-3-butyric acid) or 2,4-D (2,4-dichlorophenoxyacetic acid) | 2 mg/L |
| pH | 5.8 |
| Gelrite | 0.3% (w/v) |

TABLE 7-continued composition of optimal medium (medium 3) for the isolation and proliferation of cambium-derived homogeneous cell line having the ability to divide

| Component | Concentration and condition |
|---|---|
| Ascorbic acid | 100 mg/L |
| Citric acid | 150 mg/L |

As shown in "C" of FIG. 1(a), after the homogeneous cell line has been was specifically induced only in the cambium using osmotic stress treatment and medium 2, the homogeneous cell line was subcultured in medium 3 as shown in Table 7. As a result, the cambium-derived homogeneous cell line having the ability to divide continually divided and proliferated, and thus after about 10-20 days of the culture, the cambium-derived homogeneous cell line having the ability to divide could be isolated. The wild ginseng cambium-derived homogeneous cell line thus isolated was allowed to proliferate again by culturing it in the same medium. "D" of FIG. 1(a) shows that the isolated cambium-specific homogeneous cell line was allowed to proliferate in medium 3 shown in Table 7.

1-5: Observation of Characteristics of Isolated Cell Line

The wild ginseng cambium-derived homogeneous cell line was placed in a flask containing the liquid medium shown in Table 8. Then, the cell line was cultured in a rotating shaker at 100 rpm in a dark condition at 25±1° C. Herein, the subculture interval was set to 2 weeks, such that the cultured cells could always maintain high vitality in the exponential growth phase. 2,4-D in Table 8 was used for the proliferation of the homogeneous cell line derived from the cambium of the open field true wild ginseng, and IBA in Table 8 was used for the proliferation of the homogeneous cell line derived from the wild ginseng adventitious root.

Meanwhile, the ginseng cotyledon-derived callus was also cultured in medium 4 of Table 8, and the cultured callus was compared with the wild ginseng cambium-derived homogeneous cell line of the present invention.

TABLE 8

Suspension medium for *Panax ginseng* (medium 4)

| Component | Concentration and condition |
|---|---|
| Salt | Full strength MS |
| Sucrose | 3% (w/v) |
| IBA (Indole-3-butyric acid) or 2,4-D (2,4-dichlorophenoxyacetic acid) | 2 mg/L |
| pH | 5.8 |

The quantification of cell aggregation was observed under an optical microscope (biological microscope CX31, Olympus, Japan). As a result, it was observed that, as shown in Table 9 below, more than 95% of cells of the open field true wild ginseng cambium-derived cell line treated with 2,4-D according to the present invention were present at the single cell level during suspension culture, and more than 60% of cells of the adventitious root cambium-derived cell line treated with IBA according to the present invention were also present at the single cell level, suggesting that the cell line according to the present invention is characterized in that it is present at the single cell level during suspension culture. Also, as shown in "A" of FIG. 1(b), it could be observed that the open field true wild ginseng cambium-derived cell line treated with 2,4-D and the adventitious root cambium-derived cell line treated with IBA were all morphologically characterized by multiple vacuoles and were in an undifferentiated state. On the other hand, in the ginseng cotyledon-derived callus (Biological Resource Center KCTC PC10224), multiple vacuoles were not observed, and single large vacuole was observed as shown in "B" of FIG. 1(b).

TABLE 9

The type of cell aggregates of *Panax ginseng* long-term cultures

| Large cell aggregates | Moderate cell aggregates | Small cell aggregates | Single cell population | Explant source |
|---|---|---|---|---|
| 90% | 7% | 2% | 1% | Cotyledon |
| 0 | 0 | 5% | 95% | Cambium (treated with 2,4-D) |
| 5% | 10% | 25% | 60% | Cambium (treated with IBA) |

Large cell aggregates, size higher than $1.5 \times 10^3$ μm;
Moderate cell aggregates $1 \times 10^3$ μm;
Small cell aggregates $4 \times 10^2$ μm < size < $1 \times 10^3$ μm Meanwhile, in order to examine the possibility of scale-up culture, each of the ginseng cotyledon-derived callus and the wild ginseng cambium-derived homogeneous cell line of the present invention was cultured in an airlift bioreactor (Sung-Won Cytec, Korea) having an internal volume of 3 L. The medium used in the culture was the liquid medium shown in Table 8 and was maintained in a dark condition at 25±1° C.

As a result, as shown in Table 10 below, the doubling time of the ginseng cotyledon-derived cell culture was 21 days in the flask whereas 28 days in the reactor. In other words, it was seen that, when cultured in the flask, the cambium-derived homogeneous cell line according to the present invention showed about 3-5-fold higher growth rate compared to cell lines derived from other tissues, and when cultured in the reactor, the cambium-derived homogenous cell line according to the present invention showed 5-9-fold higher growth rate compared to cell lines derived from tissues other than the cambium. This is believed to be because cell viability rapidly decreased due to growth ring production in the reactor, plant cell aggregation during culture, and the sensitivity of hard cell walls to shear stress.

Meanwhile, the doubling time of the open field true wild ginseng cambium-derived cell culture treated with 2,4-D according to the present invention was 3-4 days in the reactor, and the doubling time of the wild ginseng adventitious root-derived homogeneous cell culture treated with IBA was 5-6 days in the reactor, which did not differ from those in the flask or was rather shortened compared to those in the flask. The cambium-derived homogeneous cell culture formed a very small growth ring area in the bioreactor, and the ring on the inner wall was simply eliminated, when a simple stimulus was applied to the bioreactor to shake the medium. Also, it was shown that the cell line of the present invention had low aggregation and contained multiple vacuoles, and thus had low sensitivity to shear stress, so that cell viability did not decrease.

In other words, it was seen that the cambium-derived cell line according to the present invention had low sensitivity to shear stress resulting from shaking in the bioreactor for scale-up culture, and thus could be produced rapidly in large amounts in the bioreactor. Accordingly, it could be seen that the cambium-derived cell line according to the present invention had 5-9-fold lower sensitivity to shear stress compared to cell lines derived from tissues other than the cambium.

TABLE 10

Doubling time of wild ginseng cambium-derived cell line and cotyledon-derived cell line in liquid suspension culture and bioreactor

| | Doubling time (day) | |
|---|---|---|
| Explant source | flask | Bioreactor |
| Cotyledon | 21 | 28 |
| Cambium (treated with 2,4-D) | 5 | 3~4 |
| Cambium (treated with IBA) | 7 | 5~6 |

Meanwhile, the ginseng cotyledon-derived heterogeneous callus (biological resource center KCTC PC10224) and the cambium-derived homogeneous cell line were cryopreserved. A suspension culture was incubated for 6-8 days, and a cryopreservative was a medium containing 0.5M glycerol (DUCHEFA, The Netherlands), 0.5M DMSO (DUCHEFA, The Netherlands) and 1M sucrose (DUCHEFA, The Netherlands) and was transferred into a 5-ml cryovial (Duran, USA). The amount of cells inoculated into the cryopreservative was 200 mg/ml. The suspended cells treated with the cryopreservative were frozen by maintaining them in a freezer for 30 minutes, storing them in a deep freezer for 3 hours, and then soaking them in liquid nitrogen.

Then, for thawing, the cultured cells maintained in liquid nitrogen for 20 minutes or more were taken out, placed in a constant-temperature water bath at 40° C. and thawed for 1-2 minutes. For cell regrowth, the cell suspension was filtrated through a sterilized funnel and filter paper. The filtrated cells were applied on a solid growth medium including filter paper, and they were stabilized at room temperature for 30 minutes, and then transferred to a fresh solid growth medium.

As a result, the ginseng cotyledon-derived heterogeneous cell line did not regrow, whereas the cambium-derived homogeneous cell line started to regrow and proliferate after 4 weeks and did not show a difference in growth rate between before and after cryopreservation.

Example 2

Drying of Wild Ginseng Cambium-Derived Cell Line and Preparation of Extract of the Cell Line The wild ginseng adventitious root cambium-derived cell line of Example 1 was dried and extracted in the following manner.

(1) Preparation of Dried Cell Line
(i) The cell line from which the culture medium has been removed was freeze-dried or hot-air-dried.
(ii) The dried cell line was ground using a grinder.
(2) Preparation of Distilled Water Extract
(i) 500 g of each of the cell line, from which the culture medium has been removed, and the hot-air-dried or freeze-dried cell line, was extracted in 5000 ml of distilled water with stirring for 24 hours.
(ii) After completion of the extraction, the cell solution was centrifuged at 3,000 g for 10 minutes, and the supernatant was collected, thus obtaining a distilled water-soluble substance.
(iii) The obtained distilled water-soluble substance was concentrated under reduced pressure using a rotary vacuum concentrator
(3) Preparation of Ethanol Extract
(i) 500 g of each of the cell line, from which the culture medium has been removed, and the hot-air-dried or freeze-dried cell line, was extracted in 5000 ml of ethanol with stirring for 24 hours.

(ii) After completion of the extraction, the cell solution was centrifuged at 3,000 g for 10 minutes, and the supernatant was collected, thus obtaining a ethanol-soluble substance.

(iii) The obtained ethanol-soluble substance was concentrated under reduced pressure using a rotary vacuum concentrator.

(4) Preparation of Methanol Extract (i) 500 g of each of the cell line, from which the culture medium has been removed, and the hot-air-dried or freeze-dried cell line, was extracted in 5000 ml of methanol with stirring for 24 hours.

(ii) After completion of the extraction, the cell solution was centrifuged at 3,000 g for 10 minutes, and the supernatant was collected, thus obtaining a methanol-soluble substance.

(iii) The obtained methanol-soluble substance was concentrated under reduced pressure using a rotary vacuum concentrator.

Experimental Example 1

In Vitro Cytostatic Activity of the Cell Line Derived from Cambium of *Panax ginseng* (1)

In order to confirm a cytostatic effect to a cancer cell line of the cell line derived from cambium of *Panax ginseng*, a measurement of inhibition efficiency was carried out by adding a methanol extract of the example 2-(4) to 8 kinds of the cancer cell lines.

AsPC-1 (pancreatic cancer), A549 (lung cancer) SK-Hep1 (liver cancer), HT-29 (colon cancer), MDA-MB-231 (breast cancer), HeLa (cervical cancer), A375P (skin melanoma), Du-145 (prostate cancer) provided by KCL B (Korean Cell Line Bank) were used in this experiment, and RPM1640 and DMEN medium supplemented with 10% calf serum.

At first, each cell line was seeded on 96-well plate at different concentrations depending on a growth rate of the cell line and was cultured at 37° C. for 16-24 hours. Then, the methanol extract of example 2-(4) and an extract of the open field true wild ginseng for control group were diluted at 12 grade doses and treated thereto. The extract of open field true wild ginseng is to compare the effect of the cell line according to present invention with that of conventional open field true wild ginseng and the methanol extract of freeze-dried open field true wild ginseng was prepared by a same process with the example 2-(4) and was used.

After 72 hours, 15 µl of MTT dye solution (Promega Corp.) was added to each well and incubated for 4 hours at 37° C. Then, 100 µl of solublization solution/stop mix was treated to each well and incubation thereof was performed at 37° C. over night. An absorbance of each well was read at 570 nm after confirming whether the colored formazan product was solubilized perfectly. The absorbance was calculated by a percentage based on the solvent-treated group and was shown as a concentration of sample ($EC_{50}$) when the absorbance of sample decreases 50% compared with that of the solvent-treated group.

Figure 2:
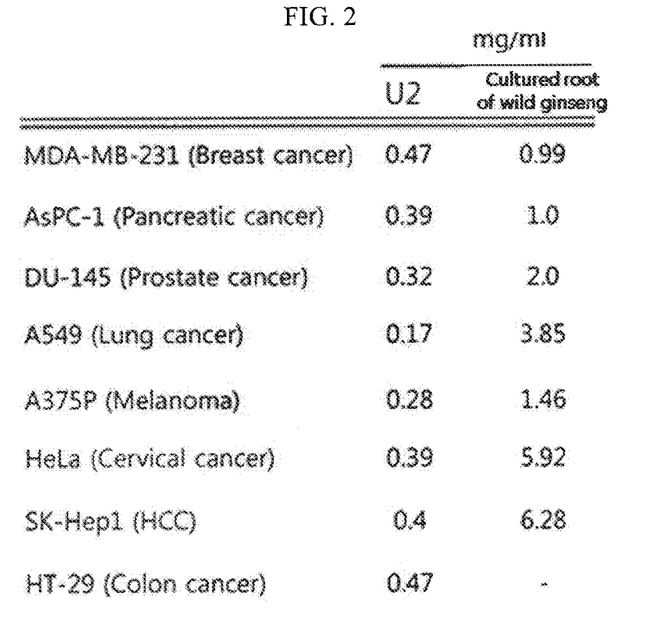
FIG. 2 shows the $EC_{50}$ value of wild ginseng cambium-derived cell line (U2) and the $EC_{50}$ value of 8 extracts of the cultured root of wild ginseng indicating an inhibitory activity of cell proliferation in cancer cell lines (HCC: Hepatocellular carcinoma; —: Not evaluated).

As the result, as shown in FIG. 2, it was confirmed that the extract of cell line derived from *Panax ginseng* according to the present invention inhibited a proliferation of 8 kinds of cancer cell line at a remarkable lower concentration than that of wild ginseng adventitious root. In particular, the extract of cell line derived from cambium of *Panax ginseng* showed an activity of inhibition to cell proliferation of colon cancer cell line from which the extract of open field true wild ginseng could not get $EC_{50}$ value even at high concentration.

Accordingly, it is confirmed that the cell line derived from cambium of *Panax ginseng* has remarkable higher cytostatic activity to cancer cell line than the extract of open field true wild ginseng and it can be used as an excellent anti-cancer drug.

Experimental Example 2

In Vitro Cytostatic Activity of the Culture Medium of the Cell Line Derived from Cambium of *Panax ginseng* (2)

In order to examine a cancer cell-killing activity of the culture medium of the cell line derived from cambium of *Panax ginseng* to cancer cell line, an experiment was performed as following procedures.

The culture medium which was isolated from the process of preparation of the extract of cell line in Example 2-(4) was used as a sample, MDA-MB-231 (breast cancer) and AsPC-1 (pancreatic cancer) provided by KCLB was used as cancer cell line groups and the RPM1640 containing 10% calf serum an d DMEM medium were used as medium in this experiment.

At first, each cancer cell line was seeded on 96-well plate at different concentrations depending on a growth rate of the cell line and was cultured at 37° C. for 16-24 hours. Then, the culture medium was diluted at 12 grade doses and treated thereto. After 72 hours, 15 µl of MTT dye solution (Promega Corp.) was added to each well and incubated for 4 hours at 37° C. Then, 100 µl of solublization solution/stop mix was treated to each well and incubation thereof was performed at 37° C. over night. An absorbance of each well was read at 570 nm after confirming whether the colored formazan product was solubilized perfectly. The absorbance was calculated by a percentage based on the solvent-treated group and was shown as a concentration of sample ($EC_{50}$) when the absorbance of sample decreases 50% compared with that of the solvent-treated group.

As a result, >7.57 mg/ml and >1.0 mg/ml of $EC_{50}$ values was obtained for MDA-MA-231 (breast cancer) and AsPC-1 (pancreatic cancer), respectively. Accordingly, it is comfirmed that the culture medium of cell line as well as the cell line itself according to the present invention has a cytostatic acitivity to cancer cell line.

Experimental Example 3

Observation of an Effect of Cancer Prevention and Treatment of Cambium-Derived Cell Line of *Panax ginseng* (1)

In order to observe an effect of cancer prevention and treatment of the cell line derived from cambium of *Panax ginseng* according to present invention, the ground dried cell line prepared in Example 2-(1) was administered in the form of powder to a patient who was diagnosed with cancer. The administration was performed orally at 1 g of its dissolved form in water, 3 times a day (morning, afternoon and night) and detail dosage and period was below. Further, it was observed that there was no side effect during the administration.

3-1: Administration to the Patient with Lymphoma

The powder of the dried cell line was administered to the patient (Ms. Kim born in 1957) who was diagnosed with lymphoma on Jan. 9, 2004 and was orally administered 3 g per day for 2 months and other anticancer therapy was not combined during the administration. To observe in vivo cancer cell-killing activity, PET-CT was performed at Hanyang University Medical Center, before administration and after 2 months of administration, respectively and results of PET-CT were compared.

Figure 3:
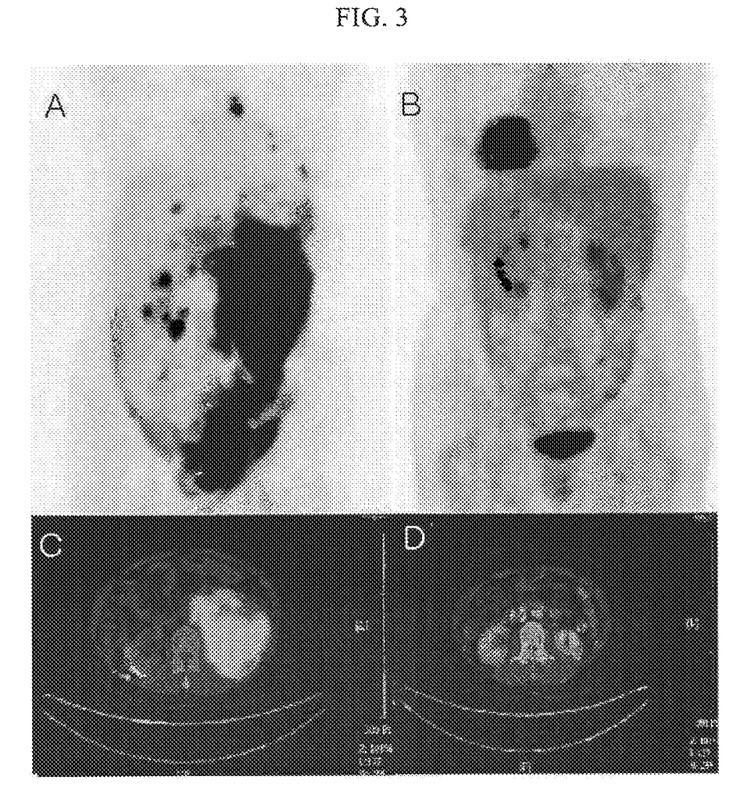
FIG. 3 is PET-CT images of patient with lymphoma before (A and C) and after (B and D) the administration of wild ginseng cambium-derived cell line.

As a result, as shown in FIG. 3, before the administration, a part showing an abnormally and widely increased metabolism was detected in the pelvic cavity and left abdominal cavity. And, malignant tumor was also shown in the pericardium, peritoneum and right kidney (FIGS. 3 A and C). On the contrary, after 2 months of administration according to this invention, it was observed that the part showing abnormally and widely increased metabolism disappeared (FIGS. 3 B and D). Therefore, this experiment results confirmed that cell line according to the present invention had an effect of prevention and treatment by the cancer cell-killing activity.

It was reported that side effects such as abnormal increases of liver level and kidney level appeared generally during an administration of an anticancer agent. In this regard, the liver level and kidney level were determined regularly during administration of cell line according to present invention as follows. As shown in Table 11, T. Bil, ALP, AST, ALT and LDH were measuring points for liver level and BUN and CRE were measuring points for kidney value and, all of which were measured in Hanyang University Medical Center. BUN and CRE was measured by serum creatinine detection method (Folin-Wu method) and AST, ALT and LDH were measured using ATBA-200FR and HITACHI 7170 Auto Analyzer and ALP was measured by serum detection method and T. Bil was measured using Asanset bilirubin test solution (Asan Pharm. Co.).

TABLE 11

|  | Normal value | 1 month after administration | 38 days after administration | 45 days after administration | 75 days after administration | 105 days after administration |
|---|---|---|---|---|---|---|
| BUN | 7~20 (mg/ml) | 17 | 11 | 14 | 9 | 13 |
| CRE | 0.6~1.8 (mg/ml) | 0.9 | 0.9 | 1.0 | 0.9 | 1.1 |
| T.Bil | 0.2~1.2 (mg/ml) | 0.3 | 0.2 | 0.2 | 0.4 | 0.2 |
| ALP | 30~110 (U/L) | 79 | 78 | 71 | 76 | 75 |
| AST | 5~40 (U/L) | 10 | 10 | 18 | 14 | 17 |
| ALT | 5~45 (U/L) | 15 | 11 | 23 | 16 | 13 |
| LDH | 60~200 (U/L) | 127 | 117 | 139 | 156 | 144 |

As a result, as shown above in Table 11, it was observed that liver and kidney levels were maintained normally, thereby suggesting that the cell line according to the present invention was free of toxicity.

3-2: Administration to Patient with Acute Myelocyte Lukemia

A patient diagnoseqd with acute myelocyte lukemia (Ms. Lee born in 1995) was orally administered 3 g per day for 8 months. Furthermore, to verify in vivo treatment effect of cancer, leukocyte and platelet counts were measured before administration and after 1 month of administration using celldyn3000 automatic blood analyzer (Abbott, wiesbaden, Germany) according to the manual of the manufacturer.

TABLE 12

|  | Leukocyte counts | Platelet counts |
|---|---|---|
| Normal value | (4,000~10,000/mm$^3$) | (141,000~316,000/mm$^3$) |
| September 1st | 600 | 73000 |
| September 2$^{nd}$ | 500 | 42000 |
| September 3$^{rd}$ | 400 | 24000 |
| September 4$^{th}$ | 400 | 52000 |
| September 5$^{th}$ | 500 | 36000 |
| September 6th | 400 | 22000 |
| September 7$^{th}$ | 500 | 16000 |
| September 8$^{th}$ | 500 | 58000 |
| September 9$^{th}$ | 300 | 40000 |
| September 10$^{th}$ | 300 | 27000 |
| September 11$^{th}$ | 400 | 40000 |
| September 12th | 600 | 26000 |
| September 13th (The date on which the administration of the cell line began) | 300 | 13000 |
| September 14$^{th}$ | 400 | 51000 |
| September 15$^{th}$ | 400 | 33000 |
| September 16$^{th}$ | 400 | 16000 |
| September 17$^{th}$ | 400 | 50000 |
| September 18$^{th}$ | 600 | 30000 |
| September 19$^{th}$ | 1000 | 23000 |
| September 20$^{th}$ | 1700 | 18000 |
| September 21$^{st}$ | 1400 | 57000 |
| September 22$^{nd}$ | 6700 | 41000 |
| September 23$^{rd}$ | 3900 | 45000 |
| September 26$^{th}$ | 3400 | 121000 |
| September 27$^{th}$ | 4400 | 117000 |
| September 28$^{th}$ | 3400 | 142000 |
| September 29$^{th}$ | 3000 | 164000 |
| October 2$^{nd}$ | 3000 | 165000 |
| October 17th | 4400 | 200000 |

Figure 4:
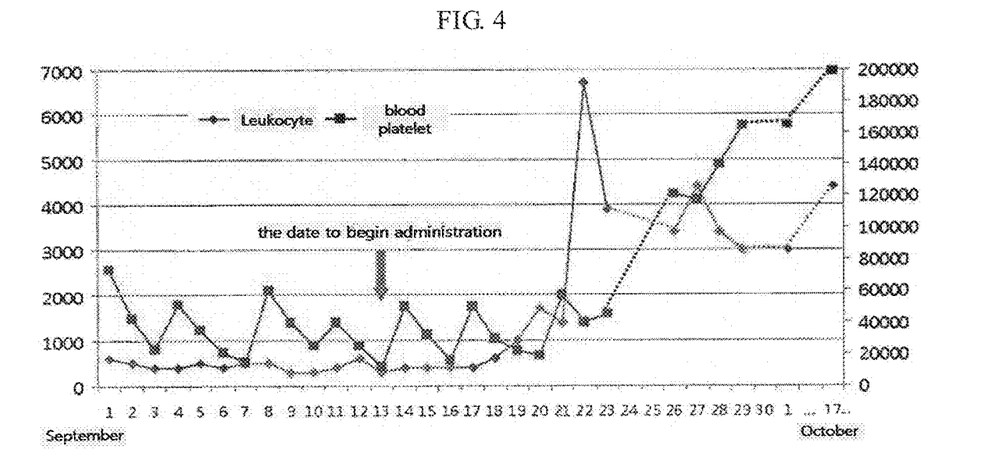
FIG. 4 is graph showing leukocyte count and blood platelet count of patient with acute myeloid leukemia according to administration duration of wild ginseng cambium-derived cell line.

As shown above in FIG. 4 and Table 12, the leukocyte counts before administration was 2,000/mm$^3$ and, the leukocyte counts increased dramatically after 9 days of administration. After 1 month of administration, the leukocyte and platelet counts were detected at normal levels (normal range of leukocyte counts: 4,000~10,000/mm$^3$; normal range of platelet counts: 141,000~316,000/mm$^3$). Accordingly, it can be confirmed that the cell line according to present invention is effective in alleviation and treatment of leukemia.

3-3: Administration to Patient with Acute Lymphoblastic Leukemia

A patient diagnosed with acute lymphoblatic lukemia (Mr. Choi born in 2001) was orally administered 3 g per day for 14 months. Furthermore, to verify in vivo treatment effect of cancer, hemoglobin levels were measured before administration and after 14 month of administration using celldyn3000 automatic blood analyzer (Abbott, wiesbaden, Germany) according to the manual of the manufacturer.

TABLE 13

|  | Hemoglobin levels |
|---|---|
| (Normal value) | (13.6~17.4 gm/dl) |
| Before administration | 3.6 gm/dl |
| After administration | 12.8 gm/dl |

As shown above in Table 13, hemoglobin levels after administration increased to normal levels compared to levels before administration.

Leukemia is based on an immature cell proliferation without entering cell differentiation stage due to a halt of certain step during differentiation process and immature cells having regular immunological phenotype proliferate in leukemia (In-sang Chun, Medical postgraduates 33, 2005). Acute lymphoblatic lukemia causes a decrease in normal blood cell levels due to a cancerous proliferation of precursor cell of leukocytes, immature cells, which results in recurrent anemia, hemorrhage, and infections, etc. This also causes a pain of bones and hypertrophy of liver and spleen, etc due to invasion of organ and results in organ injuries.

Before the administration, hemoglobin level of the patient was only 3.6 gm/dl, suggesting that the patient suffered from acute anemia. However, after administration of the cell line according to the present invention, hemoglobin levels were measured at 12.8 gm/dl, increased to normal levels, suggesting that the symptom of the leukemia was relived. Therefore, it was confirmed that the administration of the cell line according to the present invention was effective in alleviation of the leukemia.

In addition, other anticancer therapy was also combined during the oral administration. However, the anticancer therapy was performed continously from the time of initial diagnosing with leukemia, thereby suggesting that the anticancer therapy did not affect the comparison of results between before and after administration.

3-4: Administration to Patient with Lung Cancer (1) A patient (Ms. Youn born in 1939) diagnosed with lung cancer on Jul. 3, 2006 was orally administered 3 g per day for 13 months and other anticancer therapy was not combined. To observe in vivo cancer cell-killing activity, PET-CT was performed at Seoul National University Hospital, before administration and after 13 months of administration, respectively and results of PET-CT were compared.

Figure 5:
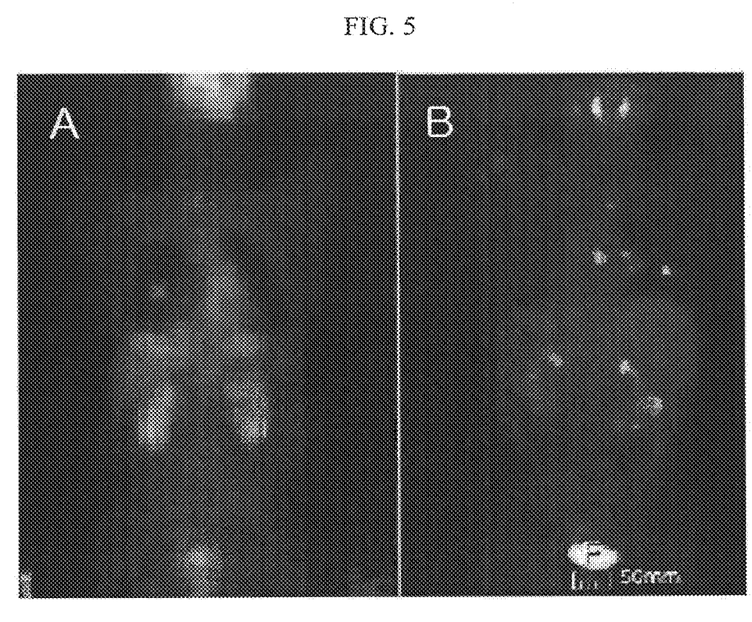
FIG. 5 is PET-CT images of patient with lung cancer before (A) and after (B) administration of wild ginseng cambium-derived cell line.

As a result, as shown in FIG. 5, when comparing between results before administration (FIG. 5A) and after administration (FIG. 5B), it was observed that an opacity decreased. Therefore, it was judged that a size of the tumor also decreased.

Accordingly, this experiment results confirm that cell line according to the present invention has an effect of prenvetion and treatment by the cancer cell-killing activity.

(2) In addition, a 62 year-old lung cancer patient (Mr. J., born in 1946) who received anticancer therapy (avastin, Genentech Inc.) was administered with the cell line according to the present invention 3 g per day for 3 months. To observe cancer cell-killing activity, a diameter of tumor was measured by CT.

As a result, it was observed that the diameter of tumor decreased from 7 cm (before administration) to 5.6 cm (after administration). Therefore, this experiment results confirmed that cell line according to the present invention had the cancer cell-killing activity.

In addition, avastin administration was also combined during the oral administration. Before the oral administration of the cell line, the size of tumor had increased continusly in spite of the avastin administration alone, thereby suggesting that the anticancer therapy did not affect the comparison of results between before and after administration.

3-5: Administration to Patient with Rectal Cancer

A patient (Ms. Kwon born in 1949) diagnosed with rectal cancer on Nov. 13, 2007 was orally administered 3 g per day and other anticancer therapy was not combined. To observe in vivo cancer cell-killing activity, PET-CT was performed at Chonbuk National University Hospital, before administration and after 49 days of administration, respectively and results of PET-CT were compared.

Figure 6:
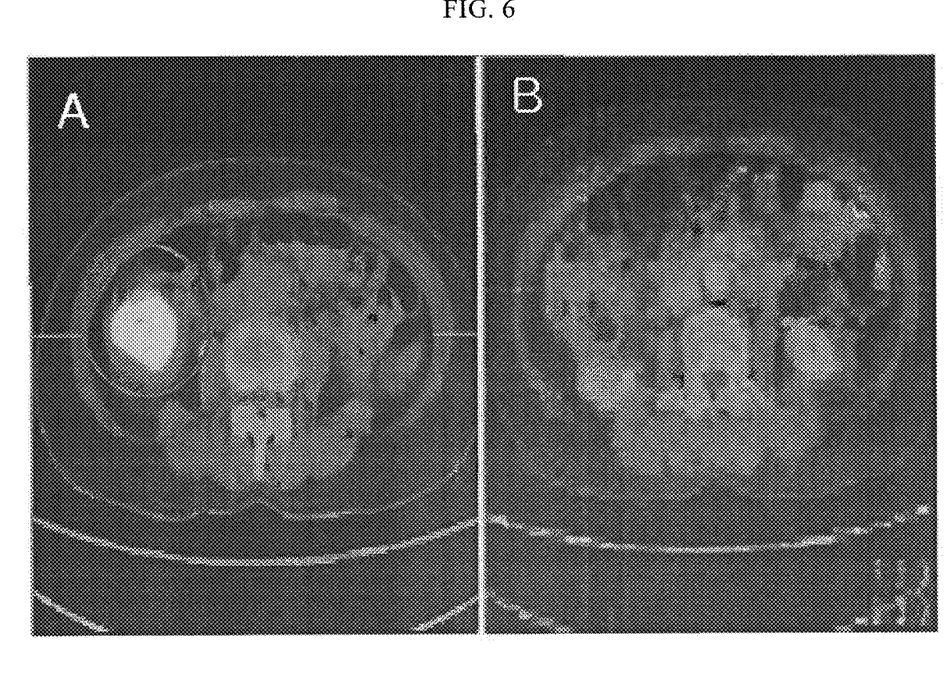
FIG. 6 is PET-CT images of patient with rectal cancer before (A) and after (B) administration of wild ginseng cambium-derived cell line.

As a result, as shown in FIG. 6, when comparing between results before administration (FIG. 6A) and after administration (FIG. 6B), it was observed that an opacity decreased. Therefore, it was judged that cancer cells were killed.

Accordingly, it is confirmed that cell line according to the present invention has an effect of prenvetion and treatment by the cancer cell-killing activity.

3-6: Administration to Patient with Gastric Cancer

A patient (Mr. Lee born in 1967) diagnosed with gastric cancer on Oct. 5, 2007 was orally administered 3 g per day and other anticancer therapy was not combined. To observe in vivo cancer cell-killing activity, size of tumor was measured using gastro-fiberscope at Ulsan Hospital, before administration and after 4 months of administration, respectively and results thereof were compared.

Figure 7:
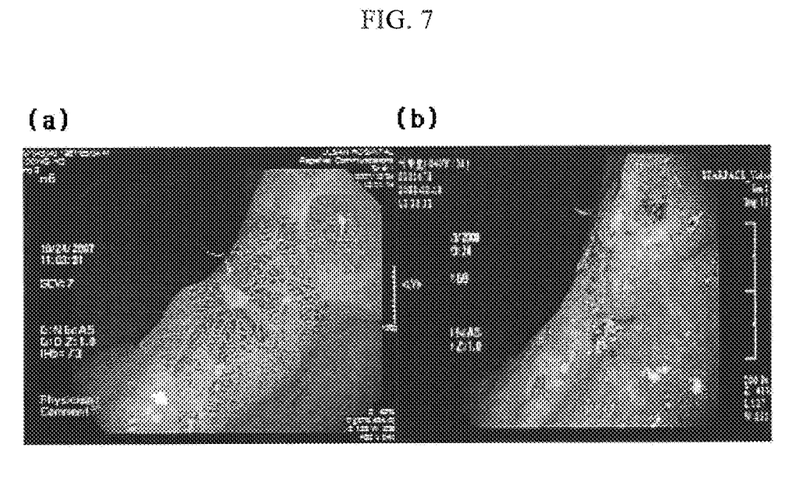
FIG. 7 is images using gastro-fiberscope of patient with rectal cancer before (A) and after (B) administration of wild ginseng cambium-derived cell line.

As a result, as shown in FIG. 7, the size of the tumor was 7 cm at the time of beginning administration (FIG. 7 (*a*)) and that was 2 cm after 4 months of administration (FIG. 7 (*b*) and thus, the size of tumor decreased drastically.

Accordingly, it is confirmed that cell line according to the present invention had an effect of prenvetion and treatment by the cancer cell-killing activity.

Experimental Example 4

Observation of an Effect of Cancer Prevention and Treatment of Cambium-Derived Cell Line of *Panax ginseng* (2)

In order to observe an effect of cancer prevention and treatment of the cell line derived from cambium of *Panax ginseng* according to present invention, the ground dried cell line prepared in Example 2-(1) was administered in the form of powder to a patient who was diagnosed with a cancer. The administration was performed orally at 1 g of its dissolved form in water, 3 times a day (morning, afternoon and night). Further, it was observed that there was no side effect during the administration.

The administration was started on Jul. 1, 2008 and, after about 1 year, chest CT was conducted on Jul. 15, 2009 at Dongsan Medical Center of Keimyung University to observe an effect of cancer prevention and treatment of the cell line derived from cambium of *Panax ginseng* according to present invention. As a result, it was observed that a size of speculated mass in LLL lateral basal segment was 26×20 mm before administration and it dramatically decreased to 14×14 mm thereafter. Further, the size of the multiple metastatic nodules in both lungs was noticeably decreased.

Accordingly, it is confirmed that the cell line derived from cambium of *Panax ginseng* according to present invention decreased the size of cancerous tumors and thereby the cell line is effective in prevention and treatment of cancer.

Example of Preparation 1

Preparation of Pharmaceutical Formulations

Formulation 1: Preparation of Tablet Formulation 100 mg of the cell line extract prepared in Example 2 was mixed with 100 mg of maize starch, 100 mg of lactose and 2 mg of magnesium stearate, and the mixture was compressed into a tablet according to a conventional tableting method.

Formulation 2: Preparation of Capsule Formulation 500 mg of the cell line extract prepared in Example 2 was filled in a soft gelatin capsule to prepare a capsule formulation.

Formulation 3: Preparation of Syrup Formulation 1 g of the cell line prepared in Example 1 was mixed with 10 g of isomerized sugar, 5 g of mannitol and a suitable amount of purifyied water, and the mixture was prepared into 100 ml of a syrup formulation according to a conventional method.

Formulation 4: Preparation of Injection Solution 200 mg of the cell line extract prepared in Example 2 was heated and dissolved in 200 mg of physiological saline containing polyoxyethylene hydrogenated castor oil, thus preparing an injection solution containing the mixed extract at a concentration of 0.1%.

Example of Preparation 2

Preparation of Functional Food—Preparation of Functional Beverage

Preparation 1: 200 mg of the cell line prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Preparation 2: 200 mg of the cell line extract prepared in Example 2 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

INDUSTRIAL APPLICABILITY

As described above, the cell line according to the present invention, a lysate thereof, an extract thereof and a culture medium thereof are derived from a natural and have minimized side effects compared to the conventional therapeutic drugs, and thus are safe for the human body. Also, they are involved directly in the growth of cancer to induce cancer cell death effectively, and show anticancer activity of inhibiting or reducing the formation of tumor or the growth of tumor, Accordingly, the cell line, the lysate thereof, the extract thereof and the culture medium thereof are useful for the prevention, treatment and alleviation of cancer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents.

What is claimed is:

1. A method of treating cancer in a subject, comprising orally administering to the subject, a composition in an oral dosage form comprising 3 g per day of a dried, ground cell line for a therapeutically effective period of time, wherein the cell line is obtained from the cambium of the storage root tissue of *Panax ginseng* by culturing said cambium-containing storage root tissue of *Panax ginseng* in a medium containing indole-3-acetic acid (IAA) to induce a cambium-derived cell line, wherein an osmotic stress is applied to the cambium-containing storage root tissue before or during the culture, and wherein the cell line is in an innately undifferentiated state and homogeneous.

2. The method according to claim 1, wherein the cell line is additionally characterized in that: (a) it is present at a single cell level during suspension culture; (b) it has low sensitivity to shear stress in a bioreactor compared to cell lines derived from tissues other than the cambium of *Panax ginseng*; (c) it has a higher growth rate than those of cell lines derived from tissues other than the cambium of *Panax ginseng* and is cultured stably; and (d) it is morphologically characterized by the presence of multiple vacuoles.

3. The method according to claim 1, wherein the induced cambium-derived cell line is proliferated in a medium containing one or more of 2,4-D (2,4-dichlorophenoxyacetic acid), picloram and indole-3-butyric acid (IBA); and thereafter collecting the cambium-derived cell line.

4. The method according to claim 1, wherein the cancer is selected from the group consisting of pancreas cancer, liver cancer, colon cancer, breast cancer, cervical cancer, skin cancer, prostate cancer, lymphoma, leukaemia, lung cancer, rectal cancer and gastric cancer.

5. A method of improving a cancer patient condition, comprising orally administering to the subject having a cancer, a composition in an oral dosage form comprising 3 g per day of a dried, ground cell line, or a beverage containing 3 g per day of a dried, ground cell line dissolved therein for a therapeutically effective period of time, wherein the cell line is obtained from the cambium of the storage root tissue of *Panax ginseng* by culturing said cambium-containing storage root tissue of *Panax ginseng* in a medium containing indole-3-acetic acid (IAA) to induce a cambium-derived cell line, wherein an osmotic stress is applied to the cambium-containing storage root tissue before or during, the culture, and wherein the cell line is in an innately undifferentiated state and homogeneous.

6. The method according to claim 5, wherein the cell line is additionally characterized in that: (a) it is present at a single cell level during suspension culture; (b) it has low sensitivity to shear stress in a bioreactor compared to cell lines derived from tissues other than the cambium of *Panax ginseng*, (c) it has a higher growth rate than those of cell lines derived from tissues other than the cambium of *Panax ginseng* and is cultured stably; and (d) it is morphologically characterized by the presence of multiple vacuoles.

7. The method according to claim 5, wherein the induced cambium-derived cell line is proliferated in a medium containing one or more of 2,4-D (2,4-dichlorophenoxyacetic acid), picloram and indole-3-butyric acid (IBA); and thereafter collecting the cambium-derived cell line.

8. The method according to claim 5, wherein the cancer is selected from the group consisting of pancreas cancer, liver cancer, colon cancer, breast cancer, cervical cancer, skin cancer, prostate cancer, lymphoma, leukaemia, lung cancer, rectal cancer and gastric cancer.

* * * * *